United States Patent [19]

Sato

[11] Patent Number: 4,503,164
[45] Date of Patent: Mar. 5, 1985

[54] ZEOLITE-TYPE CATALYST AND PROCESS FOR PREPARING SAME

[75] Inventor: Haruhito Sato, Sodegaura, Japan

[73] Assignee: Idemitsu Kosan Company Limited, Tokyo, Japan

[21] Appl. No.: 562,440

[22] Filed: Dec. 16, 1983

[30] Foreign Application Priority Data

Dec. 27, 1982 [JP] Japan ............................... 57-226551

[51] Int. Cl.$^3$ .......................... B01J 21/02; B01J 21/08
[52] U.S. Cl. ..................................... 502/202; 502/60; 423/277
[58] Field of Search ........................ 502/60, 77, 202; 423/277

[56] References Cited

U.S. PATENT DOCUMENTS

| 4,088,605 | 5/1978 | Rollmann | 423/328 T |
| 4,269,813 | 5/1981 | Klotz | 423/277 |
| 4,394,362 | 7/1983 | Miller | 423/328 T |

Primary Examiner—W. J. Shine
Attorney, Agent, or Firm—Frishauf, Holtz, Goodman & Woodward

[57] ABSTRACT

A zeolite catalyst having a double structure which comprises a core made of crystalline borosilicate and a shell made of crystalline silicon oxide. The zeolite catalyst is prepared by subjecting an aqueous solution containing a silicon compound to a hydrothermal reaction in the presence of borosilicate crystals. Various olefins are efficiently produced from methanol and/or dimethyl ether by using the zeolite catalyst. Paraxylene is also produced in a high selectivity by reacting toluene with methanol in the presence of the zeolite catalyst.

7 Claims, No Drawings

ZEOLITE-TYPE CATALYST AND PROCESS FOR PREPARING SAME

BACKGROUND OF THE INVENTION

The present invention relates to a novel zeolite catalyst and a process for the preparation thereof.

Zeolites having various structures have heretofore been prepared and uses therefor are being extensively studied. Some new types of zeolite have been developed in recent years. Japanese Patent Application Laid-Open No. 95822/1982, for example, discloses crystalline aluminosilicate which is prepared by subjecting a starting material consisting of two types of colloid having different silica/alumina ratios to a hydrothermal reaction and in which the composition of the inner portion or core is different from that of the outer portion or shell. At present the production of ethylene from methanol using the crystalline aluminosilicate as a catalyst is being studied. Japanese Patent Application Laid-Open No. 191223/1982 discloses crystalline silicate zeolite of the structure comprising the core made of crystalline silicate and the shell made of crystals containing aluminum. This crystalline silicate zeolite is used in the polymerization of olefins.

SUMMARY OF THE INVENTION

An object of the invention is to provide a zeolite catalyst which is of new structure and is useful for various reactions.

It has been found that the object can be attained by preparing the zeolite catalyst having a double structure comprising a core made of crystalline borosilicate and a shell made of crystalline silicon oxide (crystalline silicate).

The present invention relates to:

(1) a zeolite catalyst having a double structure which comprises a core made of crystalline borosilicate and a shell made of crystalline silicon oxide (crystalline silicate);

(2) a process for preparing the zeolite catalyst as described in (1) above, which comprises subjecting an aqueous solution containing a silicon compound to a hydrothermal reaction in the presence of borosilicate crystals; and (3) a process for producing olefins by bringing methanol and/or dimethyl ether into contact with the zeolite catalyst as described in (1) above, or a process for producing p-xylene by reacting toluene with methanol in the presence of the zeolite catalyst.

DETAILED DESCRIPTION OF THE INVENTION

In the zeolite catalyst of the invention, the core is made of crystalline borosilicate. Various types of crystalline borosilicate can be used, including the compounds as described in Japanese Patent Application Laid-Open Nos. 55500/1978, 7598/1980, 84313/1981, 123817/1982, and 129820/1982.

These crystalline borosilicate can be prepared by various methods. In general, they can be prepared by adding a silica source, a boron source, and a crystallizing agent to an aqueous medium, and subjecting the resulting mixture to a hydrothermal reaction.

Ammonium type crystalline borosilicate is usually prepared as follows:

An aqueous solution (Solution A) containing boric acid, concentrated sulfuric acid, and tetrapropylammonium bromide, an aqueous solution (Solution B) of water glass comprising silicon oxide, sodium oxide and water, and an aqueous solution (Solution C) of sodium chloride are prepared separately. Solutions A and B are added dropwise to Solution C, and the resulting mixture is then, if necessary, adjusted in pH, and heated in an autoclave. The reaction mixture is cooled, washed and dried to form crystalline sodium borosilicate. Treatment of the crystalline sodium borosilicate with an aqueous solution of ammonium nitrate provides the desired ammonium type crystalline borosilicate.

The zeolite catalyst of the invention has a double structure comprising, as described above, the core of crystalline borosilicate and the shell of crystalline silicon oxide. A process for the production of the zeolite catalyst according to the present invention is described below.

The crystalline borosilicate as prepared above is added to an aqueous solution containing silicon compounds such as sodium silicate, silica sol, anhydrous silicic acid (e.g., aerosil), and quartz. If necessary, a crystallizing agent, such as tetraalkylammonium halide, is added to the aqueous solution. The resulting mixture is subjected to a hydrothermal reaction and, thereafter, dried and calcined in the usual manner, whereby the desired zeolite catalyst can be obtained.

In the present zeolite catalyst of the double structure comprising the core and the shell as described above, its composition and crystal structure, for example, vary with preparation conditions. In particular, a zeolite catalyst in which the core and the shell have the same crystal structure, i.e., show the same X-ray diffraction pattern is preferred. It is also preferred for the molar ratio of silicon oxide to boron oxide in the crystalline borosilicate constituting the core to be 12:1 or more, particularly from 25:1 to 500:1, and furthermore, for the weight ratio of the shell to the core to be from 0.01:1 to 10:1, particularly from 0.1:1 to 5:1.

A zeolite catalyst satisfying the requirements as described above can be prepared as follows:

A silicon compound and a boron compound are mixed in such amounts that the molar ratio of $SiO_2$ to $B_2O_3$ is 12:1 to 500:1, and the mixture is added to water. A crystallizing agent is added thereto. The resulting mixture is then subjected to a hydrothermal reaction within a pH range of from 8.5 to 10.5 at a temperature of from 100° to 250° C. for a period of from 6 hours to 3 days and, thereafter, dried to form crystalline borosilicate. In combination with this crystalline borosilicate, a silicon compound and a crystallizing agent (molar ratio of the silicon compound to the crystallizing agent: 100:1 to 5:1) were added to water. The resulting mixture is then subjected to a hydrothermal reaction within a pH range of from 8.5 to 10.5 at a temperature of from 100° to 250° C. for a period of from 6 hours to 2 days and, thereafter, dried and calcined, whereby the desired zeolite catalyst can be prepared.

Various compounds can be used as crystallizing agents, including organic cations such as alkylammonium salts, amines such as monoamines and diamines, carboxylic acids, ketones, and alcohols such as monohydric alcohols and dihydric alcohols.

The thus-prepared zeolite catalyst is molded in itself or, if necessary, in admixture with binders such as alumina sol. Although the zeolite catalyst of the invention can be widely used in the conversion reaction of various hydrocarbons, it can be effectively utilized in the production of olefins such as ethylene from methanol and/or dimethyl ether, or in the production of p-xylene from toluene and methanol.

In producing olefins from methanol and/or dimethyl ether, the starting material (methanol and/or dimethyl ether) is brought into contact with the zeolite catalyst under suitable reaction conditions. These reaction conditions are not critical and can be determined appropriately. The reaction temperature is usually from 300° to 800° C. and preferably from 400° to 700° C.; the pressure is usually from atmospheric pressure to 50 kilograms per square centimeter and preferably from atmospheric pressure to 10 kilograms per square centimeter; and the weight hourly space velocity (WHSV) is usually from 0.1 to 40 per hour and preferably from 1 to 20 per hour. This reaction converts promptly methanol and dimethyl ether into olefins such as ethylene and propylene. Furthermore, the conversion of methanol or dimethyl ether is almost 100%, and the selectivity of olefins such as ethylene and propylene is very high.

In the production of p-xylene, toluene and methanol are reacted in the presence of the zeolite catalyst under suitable reaction conditions. These reaction conditions are not critical and can be determined appropriately. In general, the molar ratio of toluene to methanol is from 20:1 to 0.5:1 and preferably from 10:1 to 1:1; the reaction temperature is from 400° to 800° C. and preferably from 500° to 700° C.; the pressure is from atmospheric pressure to 100 kilograms per square centimeter and preferably from atmospheric pressure to 50 kilograms per square centimeter; and the weight hourly space velocity (WHSV) is from 0.1 to 50 per hour and preferably from 1 to 20 per hour. This reaction produces p-xylene in a high selectivity.

The zeolite catalyst of the invention can be used in the production of olefins and p-xylene, and furthermore can be used in the production of, for example, high-octane value gasoline through conversion of hydrocarbons. Thus its industrial value is very high.

The present invention is described in greater detail with reference to the following Examples.

EXAMPLE 1

Boron oxide (0.64 gram) was dissolved in 112.5 grams of water, and 7.92 grams of concentrated sulfuric acid and 11.8 grams of tetra-n-propylammonium bromide were further dissolved therein to prepare Solution A. Separately 95 grams of water glass ($Na_2O$: 9.40% by weight, $SiO_2$: 28.95% by weight, water: 61.65% by weight) was dissolved in 112.5 grams of water to prepare Solution B.

Solutions A and B were added dropwise simultaneously to an aqueous solution of 35.6 grams of sodium chloride in 54.9 grams of water, Solution C, at room temperature over 10 minutes. The resulting mixture, Mixture D, was boiled for 1 hour and then placed in an autoclave and heated at a temperature of 170° C. for 13 hours, whereby a product, Product E, was obtained.

Then 2.05 grams of sodium hydroxide and 23.8 grams of tetra-n-propylammonium bromide were dissolved in 150 milliliters of water to prepare a solution, Solution F, and 91.6 grams of an aqueous silica sol solution (trade name: Snowtex S; a product of Nissan Kagaku Co., Ltd.; $SiO_2$ content: 30% by weight) was dissolved in 111 milliliters of water to prepare a solution, Solution G. Solutions F and G were added dropwise simultaneously to 700 milliliters of water at room temperature over 10 minutes. To the thus-prepared mixture, Mixture H, was added Product E as prepared above, and the resulting mixture was then placed in an autoclave and heated at a temperature of 170° C. for 48 hours. At the end of the time, the reaction mixture was filtered, and the solids thus obtained were washed and dried overnight at 120° C. The solids were calcined at 550° C. for 6 hours, whereby 52.4 grams of zeolite (Na type) was obtained. The zeolite had a double structure comprising the core of crystalline borosilicate and the shell of crystalline silicon oxide.

Then 30 grams of the zeolite thus prepared was added to a 5-fold weight of 1 normal aqueous ammonium nitrate solution and refluxed for 8 hours. The mixture was cooled and allowed to stand, and the supernatant liquid was removed by decantation. This procedure of heating under reflux and decantation was further repeated three times. The mixture was filtered, washed, and dried overnight at 120° C., whereby 29.5 grams of zeolite consisting of the core of crystalline borosilicate and of the shell of crystalline silicon oxide (weight ratio of shell to core: 1.05:1) was obtained.

EXAMPLE 2

The procedure of Example 1 was repeated wherein Mixtures D and H were adjusted to pH 9.5 with concentrated sulfuric acid, whereby 54 grams of zeolite consisting of the core of crystalline borosilicate and of the shell of crystalline silicon oxide (weight ratio of shell to core: 1.05:1) was obtained.

EXAMPLE 3

Alumina sol was added to the zeolite ($NH_4^+$ type) as prepared in Example 1 as a binder in such an amount that the binder content was 20% by weight. The resulting mixture was molded and dried at 120° C. for 12 hours and calcined at 550° C. for 6 hours. Then 2 grams of the zeolite catalyst as prepared above was charged in a fixed bed flow type reaction tube at atmospheric pressure where toluene and methanol were reacted for 8 hours while maintaining the temperature at 600° C. and introducing thereinto toluene and methanol (molar ratio of toluene to methanol: 4:1) at a weight hourly space velocity (WHSV) of 9.2 per hour. The results are shown in Table 1 below.

TABLE 1

| Product | Amount (wt %)* |
|---|---|
| Benzene | 1.3 |
| Toluene | 74.8 |
| p-Xylene | 17.9 |
| m-Xylene | 4.0 |
| o-Xylene | 1.5 |
| Trimethylbenzene | 0.4 |
| Ethylbenzene | 0.1 |
| | 100.0 |

*Proportion expressed in % by weight of each component in the reaction mixture

EXAMPLE 4

Alumina sol was added to the zeolite ($NH_4^+$ type) as prepared in Example 2 as a binder in such an amount that the binder content was 20% by weight. The resulting mixture was molded and dried at 120° C. for 12 hours and calcined at 550° C. for 6 hours. Then 2 grams of the zeolite catalyst as prepared above was charged in a fixed bed flow type reaction tube at atmospheric pressure where methanol was brought into contact with the zeolite catalyst for 6 hours while maintaining the temperature at 600° C. and introducing thereinto water and methanol (weight ratio of water to methanol: 1:1) at a weight hourly space velocity of 9.2 per hour. The results are shown in Table 2 below. The conversion of methanol was 99% by weight.

TABLE 2

| Product | Amount (wt %)* |
|---|---|
| CO, $CO_2$ | 0 |
| Methane | 5.7 |
| Ethylene | 16.9 |
| Ethane | 0.3 |
| Propylene | 57.4 |
| Propane | 0.5 |
| Butane | 0.6 |
| Butene | 11.1 |
| $C_5^+$ (liquid) | 7.5 |
| | 100.0 |

*Proportion expressed in % by weight of each component in the reaction mixture

What is claimed is:

1. A zeolite-type catalyst having a double structure which comprises a core made of crystalline borosilicate and a shell made of crystalline silicon oxide.

2. The zeolite-type catalyst as claimed in claim 1, wherein the core and the shell have the same crystal structure.

3. The zeolite-type catalyst as claimed in claim 1, wherein the molar ratio of $SiO_2$ to $B_2O_3$ in the crystalline borosilicate constituting the core is at least 12:1, and the weight ratio of the shell to the core is from 0.01:1 to 10:1.

4. A process for preparing a zeolite-type catalyst having a double structure comprising a core made of crystalline borosilicate and a shell made of crystalline silicon oxide, which comprises adding borosilicate crystals to an aqueous solution containing a silicon compound and then heating to cause a hydrothermal reaction whereby silicon dioxide forms on said borosilicate crystals to form said core and shell zeolite-type catalyst.

5. The zeolite-type catalyst as claimed in claim 2, wherein the molar ratio of $SiO_2$ to $B_2O_3$ in the crystalline borosilicate constituting the core is at least 12:1, and the weight ratio of the shell to the core is from 0.01:1 to 10:1.

6. The zeolite-type catalyst as claimed in claim 1, wherein the molar ratio of $SiO_2$ to $B_2O_3$ in the crystalline borosilicate constituting the core is between 25:1 and 500:1 and wherein the weight ratio of the shell to the core is from 0.1:1 to 5:1.

7. The zeolite-type catalyst as claimed in claim 2, wherein the molar ratio of $SiO_2$ to $B_2O_3$ in the crystalline borosilicate constituting the core is between 25:1 and 500:1 and wherein the weight ratio of the shell to the core is from 0.1:1 to 5:1.

* * * * *